US009004223B2

(12) United States Patent
Saltykov

(10) Patent No.: US 9,004,223 B2
(45) Date of Patent: Apr. 14, 2015

(54) CONFORMABLE DOME EAR CANAL TIP FOR A HEARING INSTRUMENT

(75) Inventor: Oleg Saltykov, Fairlawn, NJ (US)

(73) Assignee: Siemens Medical Instruments Pte. Ltd., Singapore (SG)

(*) Notice: Subject to any disclaimer, the term of this patent is extended or adjusted under 35 U.S.C. 154(b) by 0 days.

(21) Appl. No.: 14/353,311

(22) PCT Filed: Dec. 22, 2011

(86) PCT No.: PCT/US2011/066727
§ 371 (c)(1), (2), (4) Date: Apr. 22, 2014

(87) PCT Pub. No.: WO2013/095483
PCT Pub. Date: Jun. 27, 2013

(65) Prior Publication Data
US 2014/0251716 A1 Sep. 11, 2014

(51) Int. Cl.
*A61B 7/02* (2006.01)
*H04R 25/00* (2006.01)

(52) U.S. Cl.
CPC .................................... *H04R 25/656* (2013.01)

(58) Field of Classification Search
CPC ................................ H04R 25/652; A61B 7/02
USPC .................................................. 181/135, 130
See application file for complete search history.

(56) References Cited

U.S. PATENT DOCUMENTS

| | | | | |
|---|---|---|---|---|
| 6,731,772 | B1 * | 5/2004 | Byun | 381/380 |
| 7,116,793 | B2 * | 10/2006 | Seto | 381/322 |
| 7,664,282 | B2 * | 2/2010 | Urso et al. | 381/328 |
| 7,757,400 | B2 * | 7/2010 | Widmer et al. | 29/896.21 |
| 7,889,883 | B2 * | 2/2011 | Cartwright et al. | 381/380 |
| 8,638,970 | B2 * | 1/2014 | Burton | 381/380 |
| 2003/0159878 | A1 * | 8/2003 | Hakansson et al. | 181/135 |
| 2005/0123163 | A1 | 6/2005 | Oliveira et al. | |

FOREIGN PATENT DOCUMENTS

| | | |
|---|---|---|
| EP | 1594340 | 11/2005 |
| EP | 2192789 | 2/2010 |

OTHER PUBLICATIONS

International Search Report dated Aug. 29, 2012 in Internal Application No. PCT/US2011/066727, 11 pages.

* cited by examiner

*Primary Examiner* — Forrest M Phillips
(74) *Attorney, Agent, or Firm* — Peter Kendall

(57) ABSTRACT

An ear canal tip for a hearing instrument comprises a series of slits in the ear canal tip surface to allow the ear canal tip to conform to the shape of the ear canal when the ear canal tip is inserted into the ear canal.

8 Claims, 6 Drawing Sheets

CONFORMABLE DOME EAR CANAL TIP FOR A HEARING INSTRUMENT

TECHNICAL FIELD

Hearing instruments and hearing instrument components.

BACKGROUND ART PER PCT RULE 5.1(A)(ii)

U.S. Pat. No. 5,654,530 (Sauer et al.).

DISCLOSURE OF THE INVENTION (Per PCT Rule 5.1(b), see Best Mode for Carrying out the Invention, below.)

DESCRIPTION OF THE INVENTION

Figure 1:
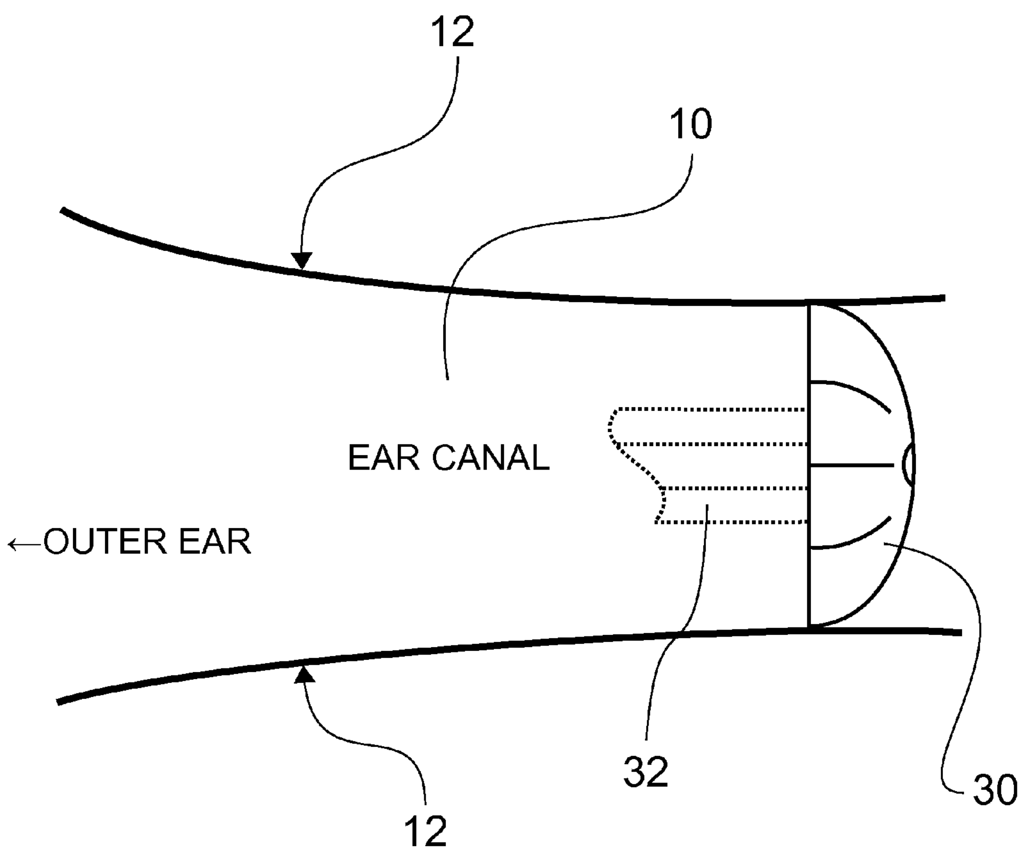
FIG. 1 is a drawing of a conformable dome ear canal tip positioned in an ear canal.

An ear canal 10 of a person, comprising ear canal walls 12, is shown in FIG. 1. As illustrated here, an ear canal tip 30, also referred to as an "ear tip," for a hearing instrument is positioned in the ear canal 10. The ear canal tip 30 comprises a sound tube 32, partially shown here in phantom, which receives and passes the sound energy generated by the hearing instrument's receiver towards the person's tympanic membrane (ear drum; not shown).

Figure 2:
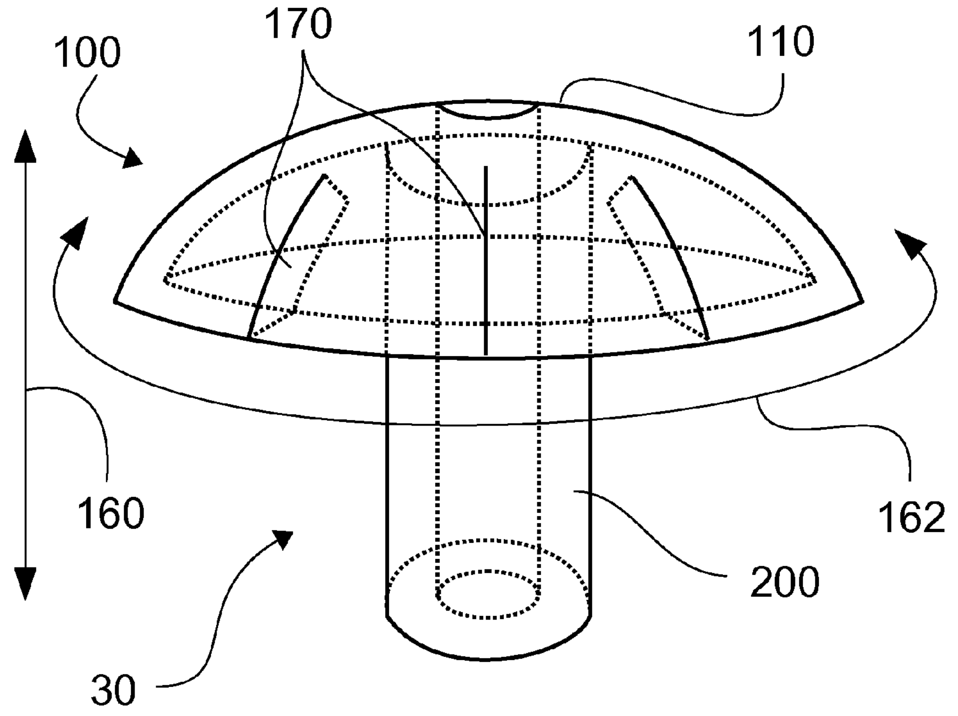
FIGS. 2 and 3 are perspective and elevation cross-sectional views, respectively, of a conformable dome ear canal tip.
Figure 3:
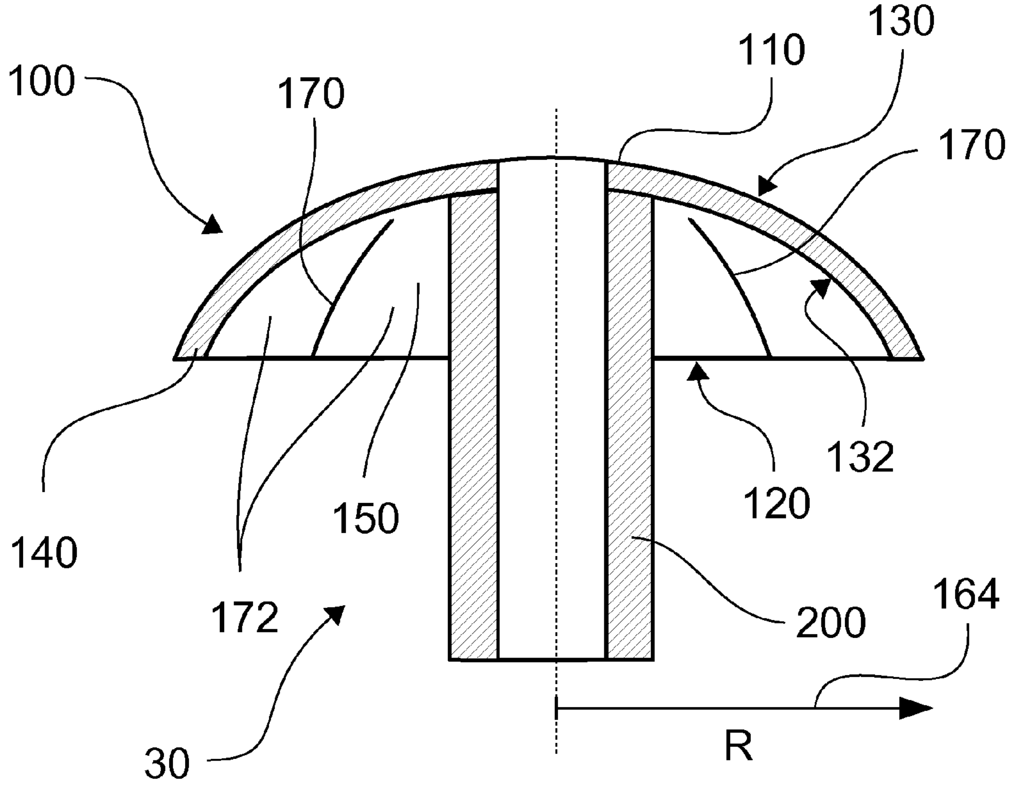

As shown in FIGS. 2 and 3, the ear canal tip 30 comprises a conformable dome 100 and a sound tube 200 through which sound passes. The conformable dome 100 comprises a top 110, a lower or bottom edge 120, an outer surface 130, an inside surface 132, a dome wall 140, a hollow interior volume 150, a vertical axis 160, a circumference 162, and a radius R 164 (the vertical dashed line represents the center line of the dome 100 and the sound tube 200).

The conformable dome 100 further comprises a plurality of slits 170 in the dome wall 140, distributed about the circumference 162 of the conformable dome 100, each slit 170 running between the lower edge 120 of the dome 100 and a terminal point between the top 110 and lower edge 120 of the conformable dome 100. The slits 170 in turn create a series of dome sections 172 about the circumference 162 of the conformable dome 100.

Figure 4:
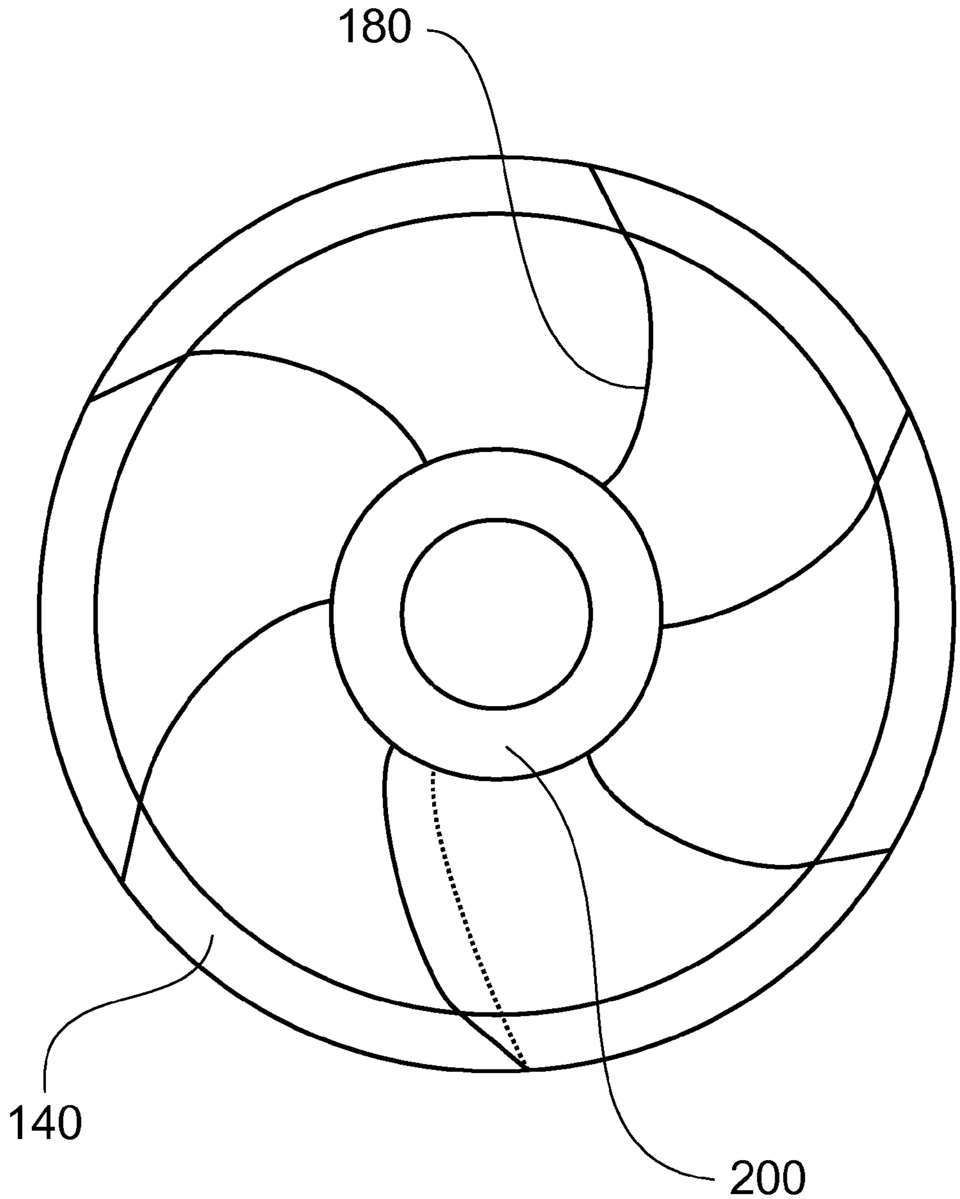
FIG. 4 is a bottom view of a conformable dome ear canal tip.

In FIGS. 2 and 3, the slits 170 radiate outwardly along the outer surface 130 of the conformable dome 100, as radial curves from points on the surface 130 to the lower edge 120. In the bottom view of FIG. 4, the slits 180 are spiral-shaped, simultaneously descending and curving towards the lower edge 120.

Figure 5:
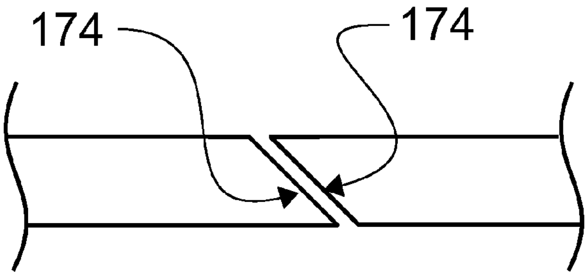
FIGS. 5-10 illustrate sections of the conformable dome.
Figure 6:
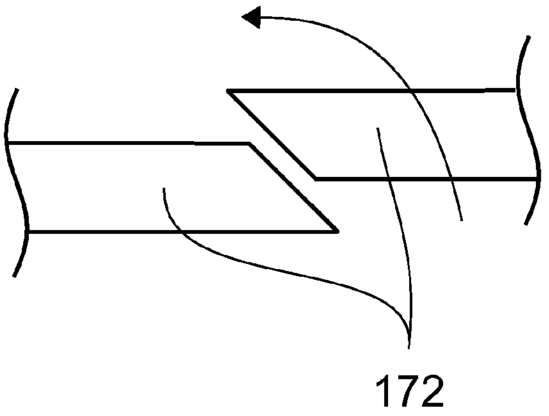
Figure 7:
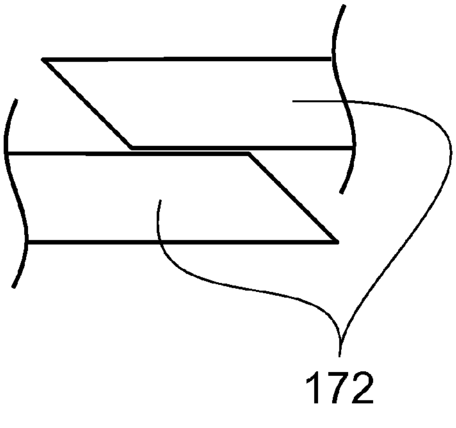
Figure 8:
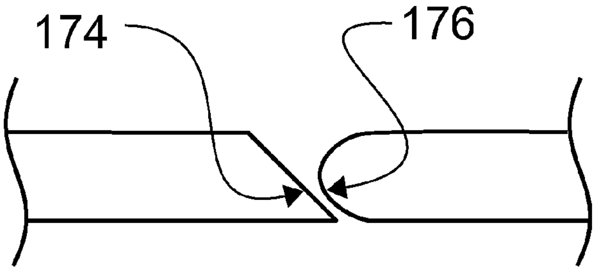
Figure 9:
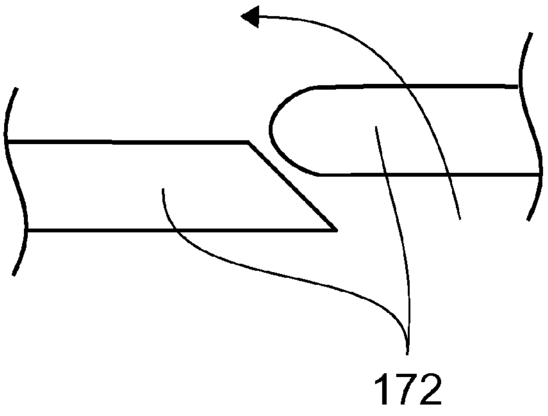
Figure 10:
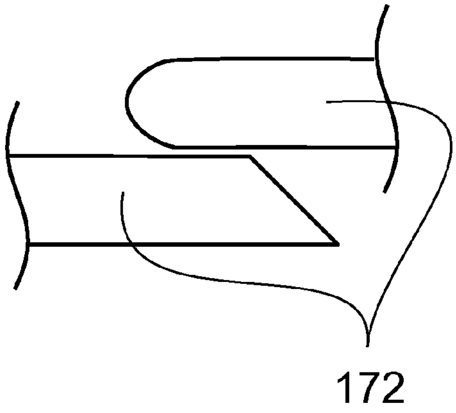

The slits 170 and 180 may have opposing beveled edges 174, as illustrated in FIGS. 5-7. When the ear canal tip 30 is inserted into the ear canal 10, the force generated by the pressure of the walls 12 of the ear canal 10 on the outer surface 130 of the conformable dome 100 and the resultant force about the circumference 162 of the conformable dome 100 will cause adjacent dome sections 172 to move towards each other. The beveled edges 174 will allow one section 172 to move behind its neighbor, as indicated by the arrow in FIG. 6 and the relative position of the sections 172 in FIG. 7. Instead of opposing beveled edges 174, one of the dome sections 172 could have a rounded surface 176, as illustrated in FIGS. 8-10.

Figure 11:
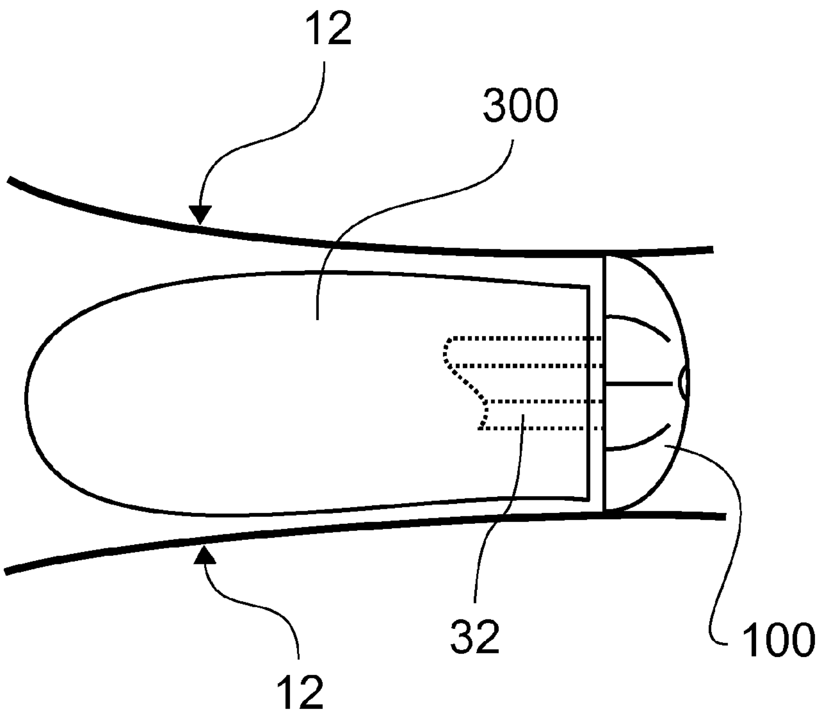
FIG. 11 illustrates the use of the conformable dome with an in-the-canal hearing instrument.
Figure 12:
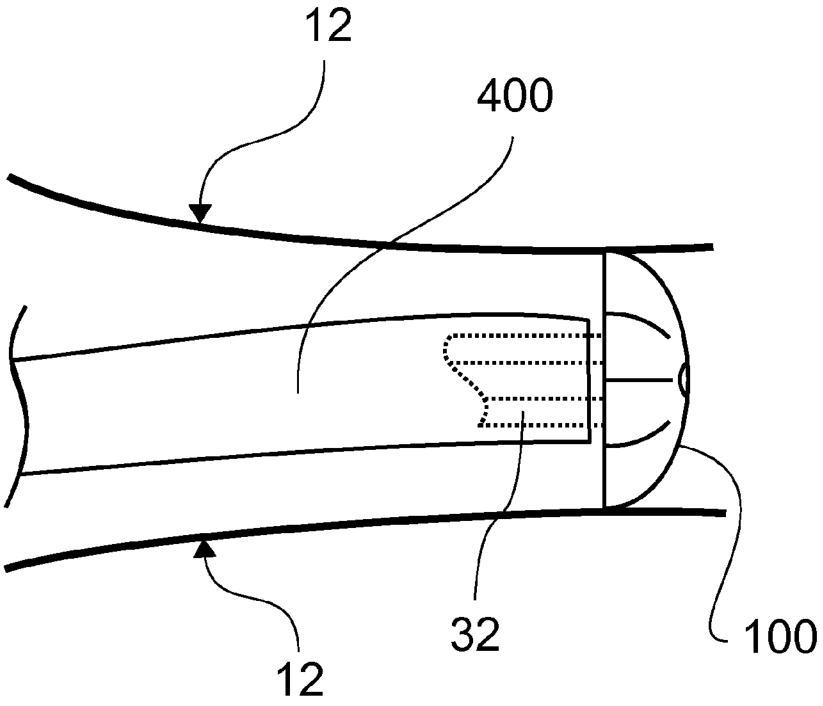
FIG. 12 illustrates the use of the conformable dome with a behind-the-ear hearing instrument comprising a receiver tube.

The conformable dome 100 may be utilized in a variety of hearing instrument configurations, including in-the-ear, in-the-canal, behind-the-ear, and receiver-in-the-canal instruments. As examples, an in-the-canal instrument 300 is shown in FIG. 11, while a receiver tube 400 for a behind-the-ear instrument is shown connected to a conformable dome 100 in FIG. 12.

INDUSTRIAL APPLICABILITY

The foregoing devices find industrial applicability in the field of hearing instruments.

What is claimed is:

1. An ear canal tip for a hearing instrument, comprising:

a conformable dome, the conformable dome comprising a dome wall, a hollow interior volume, outer and inside surfaces, a top, a lower edge, a vertical axis, a circumference, and a plurality of slits in the dome wall distributed about the circumference of the dome, each slit running between the lower edge of the dome and a terminal point between the top and lower edge of the dome;

wherein the dome wall encloses a hollow interior volume.

2. The ear canal tip according to claim 1, wherein the terminal point is near the top of the dome.

3. The ear canal tip according to claim 1, wherein each of the plurality of slits runs from the lower edge of the dome at an angle with respect to the vertical axis of the dome.

4. The ear canal tip according to claim 1, wherein each of the plurality of slits runs from the lower edge of the dome in a spiral with respect to the vertical axis of the dome.

5. The ear canal tip according to claim 1, wherein:

at least one of the plurality of slits divides the dome wall into a first wall section and a second wall section; and the first wall section has a beveled edge and the second wall section has a beveled edge opposing the beveled edge of the first wall section such that the beveled edge of the first wall section and the beveled edge of the second wall section slide across each other in opposite directions due to an applied force.

6. The ear canal tip according to claim 1, wherein:

at least one of the plurality of slits divides the dome wall into a first wall section and a second wall section; and the first wall section has a beveled edge and the second wall section has a rounded edge opposing the beveled edge of the first wall section such that the beveled edge of the first wall section and the rounded edge of the second wall section slide across each other in opposite directions due to an applied force.

7. The ear canal tip according to claim 1, wherein:

at least one of the plurality of slits divides the dome wall into a first wall section and a second wall section; and the first wall section has a beveled edge and the second wall section has a beveled edge opposing the beveled edge of the first wall section.

8. The ear canal tip according to claim 1, wherein:

at least one of the plurality of slits divides the dome wall into a first wall section and a second wall section; and the first wall section has a beveled edge and the second wall section has a rounded edge opposing the beveled edge of the first wall section.

* * * * *